United States Patent [19]

Chodnekar et al.

[11] 4,138,579

[45] Feb. 6, 1979

[54] ALKYNYLOXY-PHENYL DERIVATIVES

[75] Inventors: Madhukar S. Chodnekar, Basel; Albert Pfiffner, Pfaffhausen; Norbert Rigassi, Arlesheim; Ulrich Schwieter, Reinach; Milos Suchy, Basel, all of Switzerland

[73] Assignee: Hoffmann-La Roche Inc., Nutley, N.J.

[21] Appl. No.: 790,729

[22] Filed: Apr. 25, 1977

Related U.S. Application Data

[62] Division of Ser. No. 671,453, Mar. 29, 1976, Pat. No. 4,051,319, which is a division of Ser. No. 548,469, Feb. 10, 1975, Pat. No. 3,957,833, which is a division of Ser. No. 312,074, Dec. 4, 1972, Pat. No. 3,880,935, which is a division of Ser. No. 123,060, Mar. 10, 1971, Pat. No. 3,718,686.

[30] Foreign Application Priority Data

Mar. 25, 1970 [CH] Switzerland ..................... 4621/70

[51] Int. Cl.$^2$ ............................................. C07C 69/92
[52] U.S. Cl. ........................................ 560/64; 560/65
[58] Field of Search ................................... 560/64, 65

[56] References Cited

U.S. PATENT DOCUMENTS

| | | | |
|---|---|---|---|
| 3,868,406 | 2/1975 | Siddall | 560/64 |
| 3,880,935 | 4/1975 | Chodnekar et al. | 542/413 |
| 3,957,833 | 5/1976 | Chodnekar et al. | 260/348.43 |
| 4,051,319 | 9/1977 | Chodnekar et al. | 542/413 |

*Primary Examiner*—Jane S. Myers
*Attorney, Agent, or Firm*—Jon S. Saxe; Bernard S. Leon; William H. Epstein

[57] ABSTRACT

Alkynyl, benzyl or phenyl, ethers and esters which are ring substituted with an oxy or a thio aliphatic chain. These ethers and esters are usful in killing and preventing the proliferation of insects by upsetting their hormonal balance.

6 Claims, No Drawings

ALKYNYLOXY-PHENYL DERIVATIVES

CROSS REFERENCE TO RELATED APPLICATIONS

This application is a divisional of Ser. No. 671,453, filed Mar. 29, 1976, now U.S. Pat. No. 4,051,319, which is a divisional of Ser. No. 548,469, filed Feb. 10, 1975, now U.S. Pat. No. 3,957,833, which is a divisional of Ser. No. 312,074, filed Dec. 4, 1972, now U.S. Pat. No. 3,880,935, which is a divisional of Ser. No. 123,060, filed Mar. 10, 1971, now U.S. Pat. No. 3,718,686.

SUMMARY OF THE INVENTION

In accordance with this invention, it has been found that compounds of the formula:

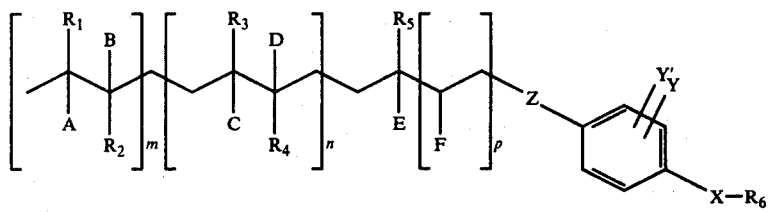

wherein $R_1$, $R_3$ and $R_5$ are methyl or ethyl; $R_2$ and $R_4$ are hydrogen or methyl; $R_6$ is lower alkynyl; A, B, C, D, E and F are individually hydrogen or A and B taken together form a carbon to carbon bond or an oxygen bridge, C and D taken together form a carbon to carbon bond, and E and F taken together form a carbon to carbon bond; Z is oxygen or sulfur; Y and Y' are hydrogen, halogen, lower alkyl or lower alkoxy; X is oxygen, —$CH_2O$— or —COO—; and m, n and p are integers of from 0 to 1, with at least one of m, n and p being 1; with the proviso that when m and n are 0, E and F are individually hydrogen, or taken together form a carbon to carbon bond or an oxygen bridge; upset the hormone balance of pests such as insects to prevent them from growing and reproducing.

The compounds of formula I are prepared by reacting a compound of the formula:

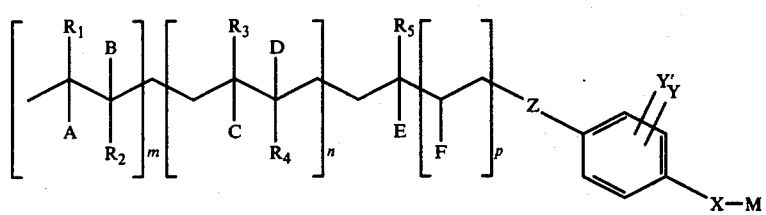

wherein $R_1$, $R_2$, $R_3$, $R_4$, $R_5$, A, B, C, D, E, F, Z, Y, Y', X, m, n and p are as above and M is an alkali metal or, where X is oxygen, an alkali metal or hydrogen; with an alkynyl halide of the formula:

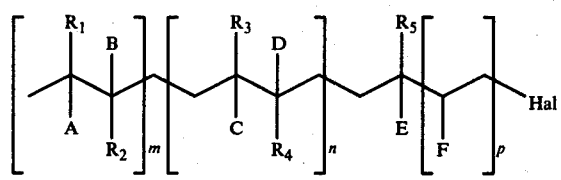

wherein $R_6$ is as above and Hal is a halogen.

The compounds of formula I are also prepared by reacting a halide of the formula:

IV wherein $R_1$, $R_2$, $R_3$, $R_4$, $R_5$, A, B, C, D, E, F, Hal, m, n and p are as above;
with a compound of the formula:

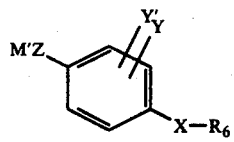

wherein $R_6$, X, Y, Y' and Z are as above and M' is an alkali metal or, where Z is oxygen, an alkali metal or hydrogen.

The compounds of formula I, wherein X is

are further prepared by reacting a compound of the formula:

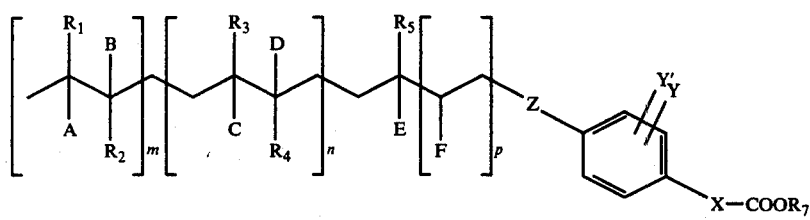

wherein $R_1, R_2, R_3, R_4, R_5$, A, B, C, D, E, F, Z, Y, Y', m, n and p are as above and $R_7$ is hydrogen, lower alkyl or aralkyl;

with an alcohol of the formula:

$$R_6—OH \qquad \text{VII}$$

wherein $R_6$ is as above.

In the case where, in the compound of formula I, A and B taken together form a carbon to carbon bond, this compound can be epoxidized to a compound of formula I wherein A and B taken together form an oxygen bridge.

DESCRIPTION OF THE PREFERRED EMBODIMENT

As used throughout this application, the term "lower alkyl" comprehends both straight-chain and branched-chain, saturated alkyl hydrocarbon groups having from 1 to 6 carbon atoms, such as methyl, ethyl, propyl, isopropyl, etc. As used herein, the term "lower alkoxy" comprehends loweralkyloxy groups wherein a "lower alkyl" is defined as above, such as methoxy, ethoxy propoxy, etc. Similarly, as used herein, the term "lower alkynyl" includes straight-chain and branched-chain, acetylenically unsaturated hydro carbon groups having from 2 to 6 carbon atoms, such as ethynyl, propargyl, butynyl, etc. As also used herein, the term "halogen" or "halo" comprehends, when not expressly stated otherwise, all four halogens, i.e., fluorine, chlorine, bromine and iodine. As further used herein, the term "alkali metal" comprehends the alkali metals of the first group of the periodic chart, such as sodium and potassium. As still further used herein, the term "aralkyl" comprehends aryl lower alkyl groups wherein "aryl" comprehends mono-nuclear aromatic hydrocarbons, such as phenyl, tolyl, etc., which can be substituted or unsubstituted in one or more positions, and polynuclear aromatic groups, such as naphthyl phenanthyl, etc., which can also be substituted or unsubstituted in one or more positions, with a nitro, halo, lower alkyl or lower alkoxy substituent, and wherein "lower alkyl" is as defined above. The preferred aralkyl group is benzene.

The compounds of formula I are useful in the control of and in combatting invertebrate animals, such as arthropods and nematodes. The compounds of formula I are especially useful against insects, particularly *Tenebrio molitor, Tineola biselliella, Carpocapsa pomonella, Leptinotarsa decemlineata, Calandra granaria, Dysdercus cingulatus* and *Ephestia kuhniella*.

In contrast to most of the known pest-control agents which kill, disable or repell the pests by acting as contact-poisons and feed-poisons, the compounds of formula I above prevent maturation and proliferation of these pests by interfering with their hormonal system. In insects, for example, the transformation to the imago, the laying of viable eggs and the development of laid normal eggs is distrubed. Furthermore, the sequence of generations is interrupted and the insects are indirectly killed.

The compounds of formula I above are practically non-toxic to vertebrates. The toxicity of the compounds of formula I is greater than, 1,000 mg/kg body weight. Moreover, these compounds are readily degraded and the risk of accumulation is therefore excluded. Therefore, these compounds can be used without fear of danger in the control of pests in animals; plants, foods; and textiles.

Generally, in controlling invertebrate animals, the compounds of formula I are applied to the material to be protected, e.g. foodstuffs, feeds, textiles, plants, in concentrations of from about $10^{-3}$ to $10^{-6}$ gm/cm$^2$ of the material to be protected. Generally, it is preferred to utilize the compounds of formula I above in a composition with a suitable inert carrier. Any conventional inert carrier can be utilized.

The compounds of formula I can, for example, be used in the form of emulsions, suspensions, dusting agents, solutions or aerosols. In special cases, the materials to be protected (e.g., foodstuffs, seeds, textiles and the like) can also be directly impregnated with the appropriate compound or with a solution thereof. Moreover, the compounds can also be used in a form which only releases them by the action of external influences (e.g., contact with moisture) or in the animal body itself. It is also possible to use the compounds in admixture with other known pesticides.

The compounds of formula I above can be used as solutions suitable for spraying on the material to be protected which can be prepared by dissolving or dispersing these compounds in a solvent such as mineral oil fractions; cold tar oils; oils of vegetable or animal origins; hydrocarbons such as napthalenes; ketones such as methyl ethyl ketone; or chlorinated hydrocarbons such as tetrachloroethylene, tetrachlorobenzene, and the like. Such sprays suitably have a concentration of the compound of formula I of 0.01% to 5% by weight, with a concentration of 0.1% being preferred. The compounds of formula I above can also be prepared in forms suitable for dilution with water to form aqueous liquids such as, for example, emulsion concentrates, pastes or powders. The compounds of formula I above can be combined with solid carriers for making, dusting or strewing powders as, for example, talc, kaolin, bentonite, calcium carbonate, calcium phosphate, etc. The compositions containing the compounds of formula I above can contain, if desired, emulsifiers, dispersing agents, wetting agents, or other active substances such as fungicides, bacteriacides, nematocides, fertilizers and the like. The materials which are to be protected act as bait for the insect. In this manner, the insect, by contacting the material impregnated with a compound of formula I above, also contacts the compound itself.

In accordance with this invention, representative examples of the preferred compounds of formula I are as follows:

1-[(1,5-dimethylhexyl)oxy]-4-(propargyloxy)benzene;

1-[(3-methyl-2-butenyl)oxy]-4-propargyloxybenzene;

p-[(1,5-dimethylhexyl)oxy]-α-propargyloxytoluene;

p-[(3-methyl-2-butenyl)oxy]-α-propargyloxytoluene;

p-[(1,5-dimethylhexyl)oxy]benzoic acid propargyl ester;

p-[(3,7-dimethyl-2,6-octadienyl)oxy]benzoic acid propargyl ester;

p-[(2,3-epoxy-3-methylbutyl)oxy]benzoic acid propargyl ester p-[(4,5-epoxy,-1,5-dimethylhexyl)oxy]benzoic acid propargyl ester;

p-[(1-ethyl-5-methyl-4-heptenyl)oxy]benzoic acid propargyl ester;

p-[(6,7-epoxy-3,7-dimethyl-2-octenyl)oxy]benzoic acid propargyl ester;

p-[(2,3-epoxy-3-methylbutyl)oxy]-α-propargyloxytoluene;

1-[(2,3-epoxy-3-methylbutyl)oxy]-4-propargyloxybenzene;

p-[(3,7,11-trimethyl-dodeca-2,6,10-trienyl)oxy]benzoic acid propargyl ester;

p-[(1,5-dimethyl-4-hexenyl)oxy]benzoic acid propargyl ester;

p-[(1,5-dimethylhexyl)thio]-α-propargyloxytoluene;

1-[(1,5-dimethylhexyl)oxy]-4-(propargyloxy)benzene;

p-[(1,5-dimethylhexyl)oxy]benzoic acid propargyl ester;

4-[(1,5-dimethylhexyl)oxy]-α-(propargyloxy)toluene;

p-[(4,5-epoxy-1,5-dimethylhexyl)oxy]benzoic acid propargyl ester;

p-[(1,5-dimethylhexyl)oxy]benzoic acid-2-pentynyl ester;

p-[(1,4,5-trimethylhexyl)oxy]benzoic acid propargyl ester;

p-[(1,5-dimethylhexyl)thio]benzoic acid propargyl ester;

p-[(3,6,7-trimethylocta-2,6-dienyl)oxy]benzoic acid propargyl ester;

p-[(3,6,7-trimethyloctyl)oxy]benzoic acid propargyl ester;

4-[(1,5-dimethylhexyl)oxy]-3-chlorobenzoic acid propargyl ester;

p-[(1,5-dimethylhexyl)oxy]vanillic acid propargyl ester;

3-methyl-4-[(3,7-dimethylocta-2,6-dienyl)oxy]benzoic acid propargyl ester;

3-bromo-4-[(6,7-dimethyl-2,6-octadienyl)oxy]-5-methoxybenzoic acid propargyl ester; and 4-[(3,7-dimethyl-2,6-octadienyl)oxy]-3,5-dimethoxybenzoic acid propargyl ester.

Especially preferred are the compounds of formula I having the formula:

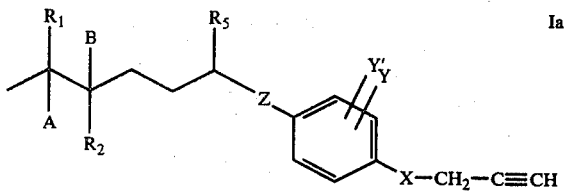

Ia wherein $R_1$, $R_2$, $R_5$, A, B, X, Y, Y' and Z are as above.

Particularly preferred are the compounds of formula Ia wherein Z is oxygen, Y is hydrogen, and A and B individually are hydrogen or taken together form an oxygen bridge. Quite particularly preferred are the following compounds of formula Ia:

1-[(1,5-dimethylhexyl)oxy]-4-propargyloxy benzene;

p-[(1,5-dimethylhexyl)oxy]benzoic acid propargyl ester;

4-[(1,5-dimethylhexyl)oxy]-α-(propargyloxy)toluene;

p-[(4,5-epoxy-1,5-dimethylhexyl)oxy]benzoic acid-propargyl ester; and p-[(1,4,5-trimethylhexyl)oxy]benzoic acid propargyl ester.

Also especially preferred are the compounds of formula I having the formula:

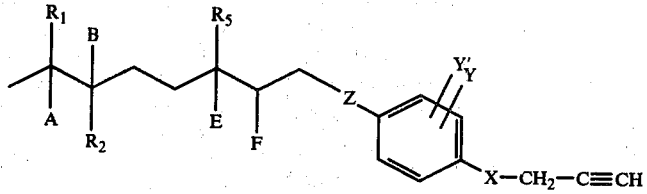

Ib wherein $R_1$, $R_2$, $R_5$, A, B, E, F, X, Y, Y' and Z are as above.

Further especially preferred compounds are the compounds of formula I wherein $R_1$, $R_2$, and/or $R_5$ are methyl; $R_2$ and/or $R_4$ is hydrogen; Z is oxygen, and/or Y and Y' are hydrogen.

One method for preparing the compounds of formula I involves reacting, in a well known manner, a compound of formula II with the alkynyl halide of formula III. This reaction is suitably conducted in an inert solvent and preferably in the presence of an aprotonic solvent. In carrying out this reaction, any conventional inert organic solvent can be utilized, with benzene, toluene, dioxane, 1,2-dimethoxymethane and tetrahydrofuran being preferred and tetrahydrofuran being especially preferred. In this reaction, any conventional aprotonic solvent may be utilized, with hexamethyl phosphoric acid triamide being preferred. In this reaction, temperature and pressure are not critical, and the reaction can be suitably carried out in a temperature range of 0° C. to the boiling point of the reaction mixture. In a preferred embodiment of this reaction, the reaction is carried out at ca 70° C., the reflux temperature of the especially preferred solvent.

Another method for preparing the compounds of formula I involves reacting, in a well known manner, the compounds of formulas IV and V. This reaction is also suitably carried out in an inert solvent, preferably in the presence of an aprotonic solvent. In carrying out this reaction, any conventional inert organic solvent can be utilized, with benzene, toluene, dioxane, 1,2-dimethoxymethane and tetrahydrofuran being preferred and tetrahydrofuran being especially preferred. In this reaction, any conventional aprotonic solvent may be utilized, with hexamethyl phosphoric acid triamide being preferred. In this reaction, temperature and pressure are not critical, and the reaction can be suitably carried out in a temperature range of 0° C. to the boiling point of the reaction mixture. In a preferred embodiment of this reaction, as in the above reaction, the preferred temperature is ca 70° C.

The reaction mixtures from the reactions of either a compound of formula II with a compound of formula III or a compound of the formula IV with a compound of formula V can be worked up in a conventional manner to obtain the compounds of formula I. A preferred method of working up includes: pouring the reaction mixture onto ice; extracting the compound of formula I with a conventional inert organic solvent, preferably diethyl ether; washing the solvent extract with water; drying the solvent and evaporating the solvent. The residual compound of formula I can be further purified by adsorption, preferably on Kieselgel or aluminum oxide.

The above reactions of a compound of formula II, wherein M is hydrogen, with an alkynyl halide of formula III and of a compound of formula V, wherein M' signifies hydrogen, with a compound of formula IV are expediently effected in the presence of an acid binding agent. In these reactions, any conventional acid binding agent may be utilized. The preferred acid binding agents are the carbonates and organic bases, such as pyridine, triethylamine and quinoline with the carbonates being especially preferred, particularly potassium carbonate. Further, in these reactions, wherein M of the compound of formula II and M' of the compound of formula V are hydrogen, the preferred solvents are acetone and methyl ethyl ketone.

Still another method for preparing the compounds of formula I, involves the esterification of an acid of the compound of formula VI where $R_7$ is hydrogen with an alcohol of formula VII. In carrying out this reaction, the acid is expediently converted, initially, in an inert solvent and in the presence of an acid binding agent into the corresponding acid halide by treatment with a halogenating agent. In this reaction, any conventional inert organic solvent can be used, with petroleum ether, benzene and hexane being preferred solvents. Also, in this reaction, any conventional acid binding agent, such as the organic bases, can be used, with pyridine, triethylamine, and quinoline being preferred and pyridine being especially preferred. Further, in this reaction, any conventional halogenating agent such as thionyl chloride, phosphorus trichloride, thionyl bromide, and phosphorus oxychloride can be used, with thionyl chloride being preferred. In this reaction, temperature and pressure are not critical, and the reaction may be suitably carried out at room temperature (25° C.).

The resulting acid halide and the alkynyl alcohol of formula VII are then reacted in an inert solvent and in the presence of an acid binding agent. In this reaction, any conventional inert organic solvent can be utilized with benzene, toluene, hexane, iso-octane, chloroform, carbon tetrachloride and ethylene glycol dimethyl ether being preferred solvents. Also in this reaction, any conventional acid binding agent may be utilized, with the organic bases, such as pyridine, triethylamine and quinoline being preferred and pyridine being especially preferred. In carrying out this reaction, temperature and pressure are not critical, and the reaction can be suitably carried out at room temperature.

Still another method for preparing the compounds of formula I involves the trans-esterification of a compound of formula VI wherein $R_7$ is alkyl or aralkyl utilizing an alcohol of formula VII. This reaction is expediently effected in an excess of the alcohol, in which case this alcohol can also serve as the solvent. However, the reaction can also be conducted in an inert organic solvent, any conventional inert organic solvent being suitable and the hydrocarbons, particularly benzene and toluene, being preferred. Temperature and pressure are not critical to this reaction, and the reaction can be expediently carried out in a temperature range between room temperature and the reflux temperature of the reaction mixture, with the reflux temperature being preferred. This reaction is preferably carried out in the presence of a catalyst such as sodium, sodium methoxide, or p-toluene-sulphonic acid.

The epoxidation of a compound of formula I wherein M is 1, Z is oxygen, and A and B taken together form a carbon to carbon bond can expediently be carried out by treating the compound in an inert solvent with a peracid. In carrying out this reaction, any conventional inert organic solvent may be utilized with the halogenated hydrocarbons such as methylene chloride or chloroform being preferred. Any conventional peracid may be utilized in this reaction. Among the preferred peracids are perbenzoic acid, peracetic acid, pertungstic acid, performic acid, m-chloroperbenzoic acid and perphthalic acid, with m-chloroperbenzoic acid being especially preferred. In carrying out this reaction, temperature and pressure are not critical, the preferred temperature range being $-10°$ C. to room temperature.

Another method for epoxidizing the compound of formula I, where M is 1, wherein Z is oxygen or sulfur, and A and B taken together form a carbon to carbon bond, involves first treating the compound with water and an N-halosuccinimide, "halo" being chlorine, bromine, or iodine, with N-bromosuccinimide being preferred to obtain a halohydrin of the formula:

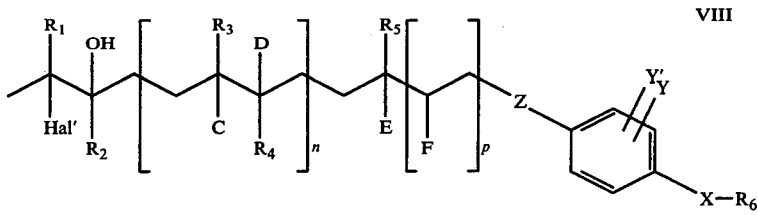

VIII wherein $R_1$, $R_2$, $R_3$, $R_4$, $R_5$, $R_6$, C, D, E, F, X, Y, Y' Z, n and p are as above, and Hal' is chlorine, bromine or iodine. In this reaction, temperature and pressure are not critical, the reaction being preferably carried out between 0° C. and 25° C. In carrying out this reaction, the unsaturated compound of formula I is preferably initially suspended in water. Then an inert organic solvent is added to the suspension to give a homogeneous concentrated solution of the compound of formula I in water and organic solvent. Any conventional inert organic solvent can be utilized in this reaction, dioxane, tetrahydrofuran and 1,2-dimethoxyethane being preferred. The N-halosuccinimide is then introduced portionwise into this homogeneous solution to yield the halohydrin of formula VIII.

These halohydrins can then be converted by the action of a base to the corresponding epoxide. In carrying out this reaction, any conventional base is suitable, with the alkali metal alkanolate being preferred, especially sodium methylate in methanol. In this reaction, temperature and pressure are not critical, the reaction being preferably carried out between 0° C. and 25° C. Any conventional inert organic solvent can be utilized in this reaction, dioxane, tetrahydrofuran and 1,2-dimethoxymethane being preferred.

The compounds of formulas II and VI can be obtained by first reacting a compound of formula IV with a compound of the formula:

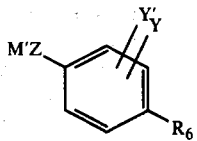

IX wherein Z, M', Y and Y' are as above; $R_6$ is hydrogen, hydroxymethyl, formyl or —$COOR_9$, and $R_9$ is lower alkyl, aryl or aralkyl.

This reaction can be carried out in the same manner described above for the reaction between the compounds of formulas IV and V to yield a compound of the formula:

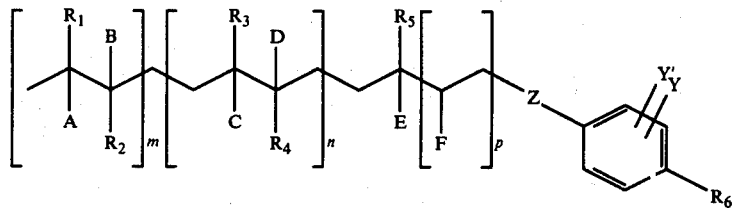

X wherein $R_1$, $R_2$, $R_3$, $R_4$, $R_5$, $R_6$, A-F, Y, Y', Z, m, n and p are as above.

The compound of formula X, wherein $R_6$ is formyl or —$COOR_9$, is then reduced to a compound of the formula:

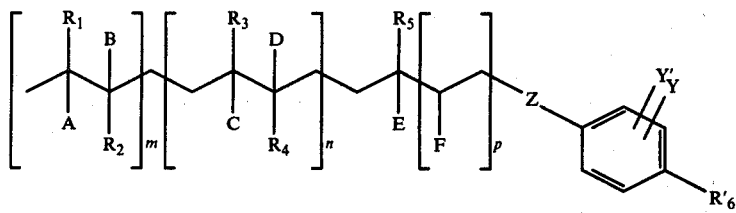

XI wherein $R_1$, $R_2$, $R_3$, $R_4$, $R_5$, A-F, Y, Y', Z, m, n and p are as above and $R_6'$ is —$CH_2OH$.

Alternatively, the compound of formula X, wherein $R_6$ is —$COOR_9$, is then saponified or the compound of formula X, wherein $R_6$ is formyl, is then oxidized to a compound of the formula:

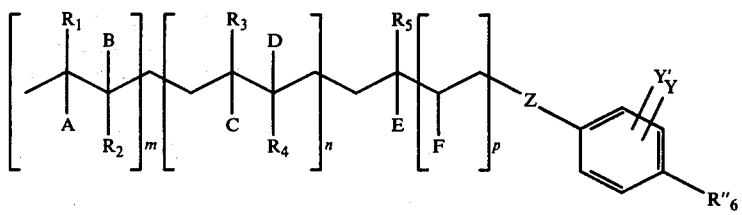

XII wherein $R_1$, $R_2$, $R_3$, $R_4$, $R_5$, A-F, Y, Y', Z, m, n and p are as above and $R_6''$ is —COOH.

The compound of formula X, wherein $R_6$ is formyl or —$COOR_9$, can be converted to the compound of formula XI, wherein $R_6$ is —$CH_2OH$, by reduction. This reduction reaction can be carried out in a conventional manner with a metal hydride, such as an alkali metal hydride, in an inert organic solvent. In carrying out this reaction, any conventional metal hydride can be used, with the preferred hydrides being mixed metal hydrides, particularly sodium borohydride or lithium aluminum hydride, and alkylated metal hydrides, particularly, dialkyl aluminum hydrides. Especially preferred hydrides are di-isobutyl aluminum hydride and bis-(methoxy-ethyleneoxy) sodium aluminum hydride. In this reaction, any conventional, inert organic solvent can be used, with the preferred solvents being: the alkanols, especially methanol, in the presence of sodium borohydride; the ethers, especially tetrahydrofuran or dioxane, in the presence of lithium aluminum hydride; and the ethers and the hydrocarbons, especially hexane, benzene or toluene, with the alkylated metal hydrides, particularly di-isobutyl aluminum hydride. Also, in carrying out this reaction, temperature and pressure are not critical, with a temperature range of —20° C. to 50° C. being preferred.

The compound of formula X, wherein $R_6$ is —$COOR_9$ can be converted to the compound of formula XII, wherein $R_6'$ is —COOH, by saponification. This saponification reaction can be carried out in a conventional manner using an alkali metal hydroxide, such as sodium or potassium hydroxide. In carrying out this reaction, temperature and pressure are not critical, and the reaction can be carried out at elevated temperature. In this reaction, any conventional inert solvent which dissolves both the alkali metal hydroxide and the compound of formula X may be utilized with diethylene glycol/water or methanol/water (1:1) being preferred.

The compound of formula X, wherein $R_6$ is formyl, can be converted to the compound of formula XII, wherein $R_6''$ is —COOH, by oxidation. This oxidation reaction can be carried out in a conventional manner using silver oxide. In carrying out this reaction temperature and pressure are not critical, and the reaction can be carried out at room temperature. The silver oxide, preferably $Ag_2O$, is preferably formed in situ in an aqueous solution of silver nitrate and caustic soda (NaOH). This reaction is carried out in water or in an organic solvent miscible with water. Any conventional organic solvent miscible with water may be used, with the following solvents being preferred: the lower alcohols, particularly methanol, ethanol and isopropanol; the ethers, particularly, 1,4-dioxane; and the ether alcohols, particularly 2-methoxy-ethanol and 2-ethoxy-ethanol.

When the compounds of formulas X, XI, and XII, wherein Z is oxygen, are unsaturated, they can, if desired, be hydrogenated in a conventional manner by, for example, hydrogenating in the presence of a conventional hydrogenation catalyst. In carrying out this reaction, temperature and pressure are not critical, a temperature range between about 25° C. and the boiling temperature of the reaction mixture and atmospheric or elevated pressures being preferred. Suitable as hydrogenation catalysts are, for example, Raney-nickel or preferably the noble metals, with palladium and platinum being especially preferred. Suitable as solvents are acetic acid ethyl ester and the alkanols such as methanol and ethanol.

When the compounds of formulas X, XI, and XII, are unsaturated, they can, if desired, be epoxidized in the same manner described above for the epoxidation of the compounds of formula I.

The compounds of formula X, wherein $R_6$ is hydroxy or hydroxymethyl, of formula XI wherein $R_6'$ is —CH$_2$OH and of formula XII, wherein $R_6''$ is —COOH, can be directly converted to the alkali metal salt of formula II. This reaction can be expediently effected by treatment with an alkali metal hydride, alkali metal alcoholate or an alkali metal hydroxide, sodium being the preferred alkali metal. The reaction is preferably carried out in the presence of an inert organic solvent. Any conventional inert organic solvent may be utilized, with dioxane, tetrahydrofuran, dimethylformamide or diethyl ether being the preferred solvents with an alkali metal hydride, with a lower alkanol, especially methanol, being the preferred solvent with an alkali metal alcoholate, and with methanol, ethanol, acetone or the like being the preferred solvent with an alkali metal hydroxide.

In the species of the compounds of formulas I, II, IV, VI, X, XI and XII of this invention, wherein the sidechain is unsaturated or epoxidized, these species exist as a cis/trans isomer mixture. The isomer mixture can be separated into the all cis or all trans isomers in a conventional manner by, for example, gas chromatography.

By this method, the isomer mixture is dissolved in an inert organic solvent, hexane, diethyl ether or acetic acid ethyl ester being preferred solvents, and then adsorbed on Kieselgel. The isomers adsorbed in different zones can be eluted with one of the aforesaid solvents or solvent mixtures and isolated.

The isomer mixtures can, in individual cases, also be separated by fractional distillation methods or possibly also by fractional crystallization methods.

The following examples illustrate the invention. All temperatures are stated in degrees centigrade. The inert gas atmosphere is nitrogen. The term "hexane/15% acetic ester" as used in Examples 5 and 41 encompasses a solution consisting of 85% hexane and 15% ethyl acetate (by volume). The term "70% bis(2-methoxy-ethoxy) sodium aluminium hydride" as used in Example 27 comprehends a benzenic solution of 70% by weight of bis(2-methoxy-ethoxy) sodium aluminium hydride. The term "80% by weight m-chlorperbenzoic acid" as used in Examples 31, 33 and 34 means that the m-chlorperbenzoic acid contains 20% m-chlorbenzoic acid and that the percentage of m-chloroperbenzoic acid present in the mixture was determined by titration in the usual manner.

EXAMPLE 1

11.8 g of a 50% by weight suspension of sodium hydride in mineral oil is washed twice in an inert gas atmosphere with 50 ml of tetrahydrofuran each time and then added to 150 ml of tetrahydrofuran. A solution of 36.5 g of hydroquinone monopropargyl ether dissolved in 80 ml of tetrahydrofuran is then added dropwise to the sodium hydride mixture. 47.5 g of 2-bromo-6-methylheptane in 80 ml of hexamethyl phosphoric acid triamide is subsequently added dropwise to the mixture. The reaction mixture is heated under reflux conditions for 2 hours, then cooled, poured onto ice and exhaustively extracted with diethyl ether. The ether extract is washed with water, dried over sodium sulfate and evaporated under reduced pressure. The residual, oily, 1-[(1,5-dimethylhexyl)oxy]-4-(propargyloxy)-benzene is purified by adsorption on Kieselgel; B.P. 150°–152° C./1 mmHg.

EXAMPLE 2

By utilizing the procedure of Example 1, by reacting hydroquinone monopropargyl ether with 3-methyl-2-butenyl bromide, there is obtained 1-[(3-methyl-2-butenyl)oxy]-4-propargyloxy-benzene; B.P. 145°–148° C./1 mmHg.

EXAMPLE 3

By utilizing the procedure of Example 1 by reacting syringic acid propargyl ester with geranyl bromide, there is obtained 4-[(3,7-dimethyl-2,6-octadienyl)oxy]-3,5-dimethoxy benzoic acid propargyl ester; $n_D^{21} = 1.5320$

EXAMPLE 4

By utilizing the procedure of Example 1, by reacting 5-bromovanillic acid propargyl ester and geranyl bromide, there is obtained 3-bromo-4-[(6,7-dimethyl-2,6-octadienyl)oxy]-5-methoxybenzoic acid propargyl ester; $n_D^{28} = 1.5440$.

EXAMPLE 5

43.5 of a 50% by weight suspension of sodium hydride in mineral oil is washed twice in an inert gas atmosphere with 100 ml of tetrahydrofuran each time and then, added to 150 ml of tetrahydrofuran. A solution of 100 g of hydroquinone in 100 ml of tetrahydrofuran is added dropwise to the sodium hydride mixture. 108 g of propargyl bromide in 150 ml of hexamethyl phosphoric acid triamide is subsequently added dropwise to the mixture. The reaction mixture is heated under reflux conditions for 2 hours, then cooled, poured onto ice and exhaustively extracted with diethyl ether. The ether extract is washed with water, dried over sodium sulfate and evaporated under reduced pressure. The residual mixture is separated by chromatography on Kieselgel. Hydroquinone dipropargyl ether is eluted with 10% acetic ester. M.P. 50° C. With hexane/15% acetic ester there is eluted hydroquinone monopropargyl ether. B.P. 100°–102° C./1.0 mmHg.

EXAMPLE 6

By utilizing the procedure of Example 5, by reacting syringic acid and propargyl bromide, there is obtained syringic acid propargyl ester, F.P. 105°–106° C.

EXAMPLE 7

By utilizing the procedure of Example 5, by reacting 5-bromovanillic acid with propargyl bromide, there is obtained 5-bromovanillic acid propargyl ester; M.P. 121°–122° C.

EXAMPLE 8

4.0 g of a 50% by weight suspension of sodium hydride in mineral oil is washed twice in an inert gas atmosphere with 25 ml of tetrahydrofuran each time and then, added to 100 ml of tetrahydrofuran. A solution of 20.6 g of p-[(1,5-dimethylhexyl)oxy] benzoic acid in 100 ml of tetrahydrofuran is then added dropwise to the sodium hydride mixture. 10 g of propargyl bromide in 40 ml of hexamethyl phosphoric acid triamide is subsequently added dropwise to the mixture. The reaction mixture is heated under reflux conditions for 2 hours, then cooled poured onto ice and exhaustively extracted with diethyl ether. The ether extract is washed with water, dried over sodium sulfate and evaporated under reduced pressure. The residual oily p-[(1,5-dimethylhexyl)oxy]benzoic acid propargyl ester is purified by adsorption on Kieselgel; B.P. 207°–210° C./1 mmHg.

EXAMPLE 9

By utilizing the procedure of Example 8, by reacting p-farnesyloxybenzoic acid with propargyl bromide, there is obtained p-farnesyloxybenzoic acid propargyl ester; B.P. 245°–250° C./0.1 mmHg.

EXAMPLE 10

By utilizing the procedure of Example 8, by reacting p-[(1,5-dimethyl-4-hexenyl)oxy]benzoic acid with propargyl bromide, there is obtained p-[(1,5-dimethyl-4-hexenyl)oxy]benzoic acid propargyl ester; $n_D^{22}$ = 1.5252.

EXAMPLE 11

By utilizing the procedure of Example 8, by reacting p-[(3,7-dimethyl-2,6-octadienyl)oxy]benzoic acid with propargyl bromide, there is obtained p-[(3,7-dimethyl-2,6-octadienyl)oxy]benzoic acid propargyl ester; B.P. 135°–137° C./0.01 mmHg.

EXAMPLE 12

By utilizing the procedure of Example 8, by reacting p-[(3,6,7-trimethylocta-2,6-dienyl)oxy]benzoic acid with propargyl bromide, there is obtained p-[(3,6,7-trimethylocta-2,6-dienyl)oxy]benzoic acid propargyl ester; $n_D^{24}$ = 1.5349.

EXAMPLE 13

By utilizing the procedure of Example 8, by reacting p-[(1,5-dimethylhexyl)oxy]-3-chlorobenzoic acid with propargyl bromide, there is obtained 4-[(1,5-dimethylhexyl)oxy]-3-chlorobenzoic acid propargyl ester; $n_D^{26}$ = 1.5155.

EXAMPLE 14

By utilizing the procedure of Example 8, by reacting p-[(1,5-dimethylhexyl)oxy]vanillic acid with propargyl bromide, there is obtained p-[(1,5-dimethylhexyl)oxy]vanillic acid propargyl ester; $n_D^{24}$ = 1.5151.

EXAMPLE 15

By utilizing the procedure of Example 8, by reacting p-[(1,4,5-trimethylhexyl)oxy]benzoic acid with propargyl bromide, there is obtained p-[(1,4,5-trimethylhexyl)oxy]benzoic acid propargyl ester; $n_D^{22}$ = 1.5050.

EXAMPLE 16

By utilizing the procedure of Example 8, by reacting p-[(1,5-dimethylhexyl)oxy]benzoic acid with 1-bromo-2-pentyne, there is obtained p-[(1,5-dimethylhexyl)oxy]benzoic acid-2-pentynyl ester; $n_D^{24}$ = 1.5078.

EXAMPLE 17

By utilizing the procedure of Example 8, by reacting p-[(1-ethyl-5-methyl-4-heptenyl)oxy]benzoic acid with propargyl bromide, there is obtained p-[(1-ethyl-5-methyl-4-heptenyl)oxy]benzoic acid propargyl ester; $n_D^{21}$ = 1.5200.

EXAMPLE 18

By utilizing the procedure of Example 8, by reacting 3-methyl-4-[(3,7-dimethylocta-2,6-octadienyl)-oxy]-benzoic acid with propargyl bromide, there is obtained 3-methyl-4-[(3,7-dimethylocta-2,6-dienyl)oxy]benzoic acid propargyl ester; $n_D^{28}$ = 1.5331.

EXAMPLE 19

13.7 g of a 50% suspension of sodium hydride in mineral oil is washed twice in an inert gas atmosphere with 70 ml of tetrahydrofuran each time and then, added to 100 ml of tetrahydrofuran. A solution of 40 g of p-hydroxybenzoic acid methyl ester in 250 ml of tetrahydrofuran is then added dropwise to the sodium hydride mixture. 50 g of 2-bromo-6-methylhept-5-ene in 80 ml of hexamethyl phosphoric acid triamide is subsequently added dropwise to the mixture. The reaction mixture is heated under reflux conditions for 2 hours, poured onto ice and exhaustively extracted with diethyl ether. The ether extract is washed with water, dried over sodium sulfate and evaporated under reduced pressure. The residual oily p-[(1,5-dimethyl-4-hexenyl)oxy]benzoic acid methyl ester is purified by adsorption on Kieselgel; $n_D^{25}$ = 1.5109.

EXAMPLE 20

By utilizing the procedure of Example 19, by reacting p-hydroxybenzoic acid methyl ester with 2-bromo-6-methyl heptane, there is obtained p-[(1,5-dimethylhexyl)oxy]benozic acid methyl ester; B.P. 132°–134° C./0.1 mmHg.

EXAMPLE 21

By utilizing the procedure of Example 19, by reacting p-hydroxybenzoic acid methyl ester with 2-bromo-5,6-dimethyl heptane, there is obtained p-[(1,4,5-trimethylhexyl)oxy]benzoic acid methyl ester; $n_D^{25}$ = 1.4938.

EXAMPLE 22

By utilizing the procedure of Example 19, by reacting p-hydroxybenzoic acid methyl ester with 3-bromo-7-methylnon-6-ene, there is obtained p-[(1-ethyl-5-methyl-4-haptenyl)oxy]benzoic acid methyl ester; B.P. 202°–205° C./12 mmHg.

EXAMPLE 23

By utilizing the procedure of Example 19, by reacting 3-methyl-4-hydroxybenzoic acid methyl ester with 1-bromo-3,7-dimethyl-2,6-octadiene, there is obtained 3-methyl-4-[(3,7-dimethyl-2,6-octadienyl)oxy]benzoic acid methyl ester; $n_D^{28}$ = 1.5248.

EXAMPLE 24

7.2 g of p-[(1,5-dimethyl-hex-4-enyl)oxy]-benzoic acid methyl ester is dissolved in 30 ml of 2-N aqueous caustic soda, diluted with 50 ml of an aqueous solution of 50% by volume methanol and heated under reflux for 1½ hours. The reaction solution is then cooled, treated with 200 ml of water and exhaustively extracted with diethyl ether. The alkaline aqueous phase is acidified with 2-N hydrochloric acid and exhaustively extracted with diethyl ether. The latter ether extract is dried over sodium sulfate and evaporated under reduced pressure. The residual p-[(1,5-dimethylhex-4-enyl)oxy]benzoic acid is purified by crystallization from benzene; M.P. 57°–59° C.

EXAMPLE 25

By utilizing the procedure of Example 24, the following acids can be obtained from their corresponding methyl esters:

p-[(1,5-dimethylhexyl)oxy]benzoic acid; M.P. 55° C.;
p-[(3,7,11-trimethyl-dodeca-2,6,10-trienyl)oxy]benzoic acid; M.P. 80°–81° C.;
p-[(3,7-dimethyl-2,6-octadienyl)oxy]benzoic acid; M.P. 118°–120° C.;
p-[(3,6,7-trimethylocta-2,6-dienyl)oxy]benzoic acid; M.P. 128°–129° C.;
p-[(1,5-dimethylhexyl)oxy]-3-chlorobenzoic acid; $n_D^{26} = 1.5231$;
p-[(1,5-dimethylhexyl)oxy]vanillic acid; M.P. 69°–70° C.;
p-[(3-methyl-2-butenyl)oxy]benzoic acid; M.P. 153°–154° C.;
p-[(1,4,5-trimethylhexyl)oxy]benzoic acid; $n_D^{21} = 1.5082$;
p-[(1-ethyl-5-methyl-4-heptenyl)oxy]benzoic acid; $n_D^{21} = 1.4891$; and
3-methyl-4-[(3,7-dimethyl-2,6-octadienyl)oxy]benzoic acid; F.P. 93°–94° C.

EXAMPLE 26

4.1 g of a 50% by weight suspension of sodium hydride in mineral oil is washed twice in an inert gas atmosphere with 25 ml of tetrahydrofuran each time and then, added to 50 ml. of tetrahydrofuran. A solution of 20 g of p-[(1,5-dimethylhexyl)oxy]benzyl alcohol in 100 ml of tetrahydrofuran is then added dropwise to this mixture. 10.3 g propargyl bromide in 40 ml of hexamethyl phosphoric acid triamide is subsequently added dropwise to the mixture. The reaction mixture is heated under reflux conditions for 2 hours, then cooled, poured onto ice and exhaustively extracted with diethyl ether. The ether extract is washed with water, dried over sodium sulfate and evaporated under reduced pressure. The residual oily p-[(1,5-dimethylhexyl)oxy]-α-propargyloxytoluene is purified by adsorption on Kieselgel; B.P. 170°–175° C./1.0 mmHg.

EXAMPLE 27

42 g of p-[(1,5-dimethylhexyl)oxy]benzoic acid methyl ester is dissolved in 250 ml of benzene and, with stirring, treated dropwise with 50 g of 70% bis(2-methoxy-ethoxy)sodium aluminum hydride. The reaction solution is further stirred at 25° C. for 5 hours and thereafter treated with water. The organic phase is separated off, dried under sodium sulfate, carefully filtered (using a filter aid) and evaporated under reduced pressure. There is obtained a residual of p-[(1,5-dimethylhexyl)oxy]benzyl alcohol; B.P. 180°–182° C./1.0 mmHg.

EXAMPLE 28

By utilizing the procedure of Example 26, by reaction p-[(3-methyl-2-butenyl)oxy]benzyl alcohol with propargyl bromide, there is obtained 1-[(3-methyl-2-butenyl)oxy]-4-propargyloxy-toluene; B.P. 146°–149° C./1 mmHg.

EXAMPLE 29

10.1 g of a 50% by weight suspension of sodium hydride in mineral oil is washed twice in an inert gas atmosphere with 50 ml of tetrahydrofuran each time and then, introduced into 100 ml of tetrahydrofuran. A solution of 32 g of p-hydroxybenzoic acid methyl ester in 200 ml of tetrahydrofuran is then added dropwise to the sodium hydride mixture. 40.5 g of 1-bromo-3-methylbut-2-ene in 80 ml of hexamethyl phosphoric acid triamide is subsequently added dropwise to the mixture. The reaction mixture is heated under reflux conditions for 2 hours, then cooled, poured onto ice and exhaustively extracted with diethyl ether. The ether extract is washed with water, dried over sodium sulfate and evaporated under reduced pressure. The residual oily p-[(3-methyl-2-butenyl)oxy]benzoic acid methyl ester is purified by adsorption on Kieselgel. M.P. 45°–46° C.

By utilizing the procedure of Example 27, p-[(3-methyl-2-butenyl)oxy]benzoic acid methyl ester is converted into p-[(3-methyl-2-butenyl)oxy]benzyl alcohol; M.P. 41°–42° C.

EXAMPLE 30

2.2 g of 50% by weight suspension of sodium hydride in mineral oil is washed twice in an inert gas atmosphere with 25 ml of tetrahydrofuran each time and then added to 30 ml of tetrahydrofuran a solution of 9.9 g of p-[(2,3-epoxy-3-methylbutyloxy)benzoic acid in 100 ml of tetrahydrofuran is then added dropwise to the sodium hydride mixture 5.5 g of propargyl bromide in 20 ml of hexamethyl phosphoric acid triamide is subsequently added dropwise to the mixture. The reaction mixture is heated under reflux conditions for 2 hours, then cooled, poured onto ice and exhaustively extracted with diethyl ether. The ether extract is washed with water, dried over sodium sulfate and evaporated under reduced pressure. The residual oily p-[(2,3-epoxy-3-methylbutyloxy)benzoic acid propargyl ester is purified by adsorption on Kieselgel; M.P. 80°–81° C.

EXAMPLE 31

3.9 g of p-[(1,5-dimethyl-hex-4-enyl)oxy]benzoic acid propargyl ester is dissolved in 150 ml of methylene chloride. The solution is treated dropwise at 0° C. with a solution of 3.0 g of 80% by weight m-chloroperbenzoic acid in 100 ml of methylene chloride. After 15 mins., the reaction mixture is successively washed with an aqueous solution of 2% by weight sodium bisulphite with an aqueous solution of 5% by weight sodium bicarbonate and with water. The organic phase is separated off, washed over sodium sulphate and evaporated under reduced pressure. The residual p-[(4,5-epoxy-1,5-dimethylhexyl)oxy]benzoic acid propargyl ester is purified by adsorption on Kieselgel; B.P. 120°–123° C./0.05 mmHg.

EXAMPLE 32

By utilizing the procedure of Example 31, 2.0 g of p-[(3,7-dimethyl-2,6-octadienyl)oxy]benzoic acid propargyl ester is converted into p-[(6,7-epoxy-3,7-dimethyl-2-octenyl)oxy]benzoic acid propargyl ester; $n_D^{24} = 1.5362$.

EXAMPLE 33

1.15 g of p-[(3-methyl-2-butenyl)oxy]-α-propargyloxy-toluene is dissolved in 40 ml of methylene chloride and cooled to 0° C. (ice-bath cooling). 1.5 g of 80% by weight m-chloroperbenzoic acid is added portionwise to this mixture and the solution is thereafter stirred at 0° C. for 2 hours. The mixture is worked up as follows: diluted with 350 ml of methylene chloride; washed with ice-cold 1-N caustic soda; washed with saturated aqueous sodium chloride solution; dried over sodium sulfate; and evaporated. By chromatography on Kieselgel, there is obtained p-[(2,3-epoxy-3-methyl-butyloxy]-α-propargyloxy-toluene; B.P. 120°-123° C./0.1 mmHg.

EXAMPLE 34

6.4 g of 1-[(3-methyl-2-butenyl)oxy]-4-propargyloxy-benzene is dissolved in 80 ml of methylenechloride and cooled to 0° C. (ice-bath cooling). 7.15 g of 80% by weight m-chloroperbenzoic acid is added portionwise to this mixture and the solution is thereafter stirred at 0° C. for 2 hours. The mixture is worked up as follows: diluted with 350 ml of methylene chloride; washed with ice-cold 1-N caustic soda; washed with saturated aqueous sodium chloride solution; dried over sodium sulfate; and evaporated. By chromatography on Kieselgel, there is obtained 1-[(2,3-epoxy-3-methylbutyl)oxy]-4-propargyloxy-benzene; M.P. 72°-73° C.

EXAMPLE 35

By utilizing the procedure of Example 26, by reacting p-[(1,5-dimethylhexyl)thio]benzyl alcohol with propargyl bromide, there is obtained p-[(1,5-dimethylhexyl)thio]-α-propargyloxy-toluene; $n_D^{29} = 1.5243$.

EXAMPLE 36

By utilizing the procedure of Example 27, p-[(1,5-dimethylhexyl)thio]benzoic acid methyl ester is converted into p-[(1,5-dimethylhexyl)thio]benzyl alcohol; $n_D^{29} = 1.5270$.

EXAMPLE 37

By utilizing the procedure of Example 19, by reacting p-thio benzoic acid methyl ester with 2-bromo-6-methylheptane, there is obtained p-[(1,5-dimethylhexyl)-thio]benzoic acid methyl ester; B.P. 168°-170° C./0.5 mmHg.

EXAMPLE 38

By utilizing the procedure of Example 8, by reacting p-[(1,5-dimethylhexyl)thio]benzoic acid and propargyl bromide, there is obtained p-[(1,5-dimethylhexyl)thio]-benzoic acid propargyl ester M.P. 130°-131° C./0.03 mmHg.

EXAMPLE 39

By utilizing the procedure of Example 24, p-[(1,5-dimethylhexyl)thio]benzoic acid methyl ester is converted into p-[(1,5-dimethylhexyl)thio]benzoic acid; M.P. 63°-65° C.

EXAMPLE 40

By utilizing the procedure of Example 8, by reacting p-[(3,6,7-trimethyloctyl)oxy]benzoic acid with propargyl bromide, there is obtained p-[(3,6,7-trimethyloctyl)oxy]benzoic acid propargyl esters; B.P. 153°-154° C./0.05 mmHg.

EXAMPLE 41

5 g of p-[(3,6,7-trimethylocta-2,6-dienyl)oxy]benzoic acid is dissolved in 20 ml of acetic ester and hydrogenated under normal pressure and at a temperature of about 25° C. in the presence of 0.2 g of platinum oxide. The hydrogenation is terminated after the uptake of 2 mols of hydrogen, and the catalyst is filtered off from the reaction mixture. The clear solution is evaporated under reduced pressure. The residual p-[(3,6,7-trimethyloctyl)oxy]benzoic acid is purified by crystallization from petroleum ether; M.P. 89°-90° C.

EXAMPLE 42

10 g of p-[(1,5-dimethylhexyl)oxy]benzoic acid is heated to 70° C. with 20 ml of thionyl chloride for 10 mins. The clear yellow-colored solution is evaporated at 50° C. under water-jet pump vacuum. After the addition of 40 ml of propargyl alcohol, the mixture is heated to 70° C. for 15 min. After evaporation in water-jet pump vacuum, the residue is chromatographed on Kieselgel, yielding p-[(1,5-dimethylhexyl)oxy]benzoic acid propargyl ester; B.P. 207°-210° C./1.0 mmHg.

EXAMPLE 43

10 g of p-[(1,5-dimethylhexyl)oxy]benzoic acid methyl ester, 30 ml of propargyl alcohol and 0.5 g of sodium methoxide are heated to reflux for ½ an hour. The excess propargyl alcohol is thereupon slowly (5 hrs.) distilled off. The residue is poured onto water and extracted with diethyl ether. The ether solution is dried with sodium sulfate and evaporated. The dark-yellow p-[(1,5-dimethylhexyl)oxy]benzoic acid propargyl ester obtained is purified over kieselgel.

EXAMPLE 44

13 g of p-[(1,5-dimethylhexyl)oxy]benzoic acid methyl ester is heated to reflux with 9 g of propargyl alcohol and 0.1 g of p-toluenesulphonic acid. The excess propargyl alcohol is thereupon slowly (5 hrs.) distilled off. The residue is poured onto water and extracted with diethyl ether. The ether phase is dried with sodium sulfate and evaporated. There is obtained dark-yellow p-[(1,5-dimethylhexyl)oxy]benzoic acid propargyl ester which is purified on Kieselgel.

The experiments described in the following examples are carried out with the following representative examples of the propargyloxy derivatives of this invention as the active substances.

(I) p-[(1,5-dimethylhexyl)oxy]-α-propargyloxytoluene (II) p-[(1,5-dimethylhexyl)oxy]benzoic acid propargyl ester (III) p-[(1,5-dimethyl-4-hexenyl)oxy]benzoic acid propargyl ester (IV) 1-[(2,3-epoxy-3-methylbutyl)oxy]benzoic acid propargyl ester (V) 1-[(1,5-dimethylhexyl)oxy]-4-(propargyloxy)benzene (VI) 1-[(2,3-epoxy-3-methylbutyl)oxy]-4-(propargyloxy)-benzene.

EXAMPLE 45

2 filter paper discs [24 cm$^2$] are sprayed with an acetonic solution of the active substance, and after drying, the discs together with an untreated paper disc and with a paper disc soaked only with acetone, are each so fixed together that there is formed a tunnel for the shelter of 10 cockroaches (*Blattella germanica*) each. The cockroaches are in the last larval stage. They remain in permanent contact with the treated paper and are provided with water and food.

The development of the larvae set out is registered daily. 100% disturbance of metamorphosis: A normal animal develops from none of the larvae

| Active substance | Amount of active substance $10^{-x}$g/cm$^2$ | Number of larvae | Number of normal imagos | Number of normal animals | Activity % |
|---|---|---|---|---|---|
| I | $10^{-4}$ | 10 | 1 | 5 | 83 |
| Control with acetone | | 10 | 10 | — | — |
| Control with acetone | | 10 | 10 | — | — |

EXAMPLE 46

A disc of cotton material [10 cm$^2$] is sprayed with an acetonic solution of the active substance, and after drying, the disc, together with an untreated disc of material and a disc of material soaked only with acetone, are each occupied by 30–60 freshly laid eggs of the meal moth (*Ephestia kuhniella*). The disc is placed in a cage and held at 25° C. and 90% rel. humidity.

The development of the eggs is registered over a few days. 100% mortality of the eggs: No development of the embryos in the eggs layed on discs of material soaked with active substance.

| Active substance | Amount of active substance $10^{-x}$g/cm$^2$ | Number of eggs | Number of larvae | Mortality % |
|---|---|---|---|---|
| I | $10^{-5}$ | 32 | 0 | 100 |
|  | $10^{-6}$ | 33 | 0 | 100 |
| II | $10^{-5}$ | 32 | 0 | 100 |
|  | $10^{-6}$ | 30 | 0 | 100 |
| III | $10^{-4}$ | 40 | 0 | 100 |
|  | $10^{-5}$ | 36 | 0 | 100 |
|  | $10^{-6}$ | 36 | 0 | 100 |
| IV | $10^{-5}$ | 47 | 0 | 100 |
|  | $10^{-6}$ | 33 | 0 | 100 |
| V | $10^{-5}$ | 44 | 0 | 100 |
|  | $10^{-6}$ | 34 | 0 | 100 |
| Control with acetone | | 50 | 50 | 0 |
| Control with acetone | | 49 | 46 | 6 |

EXAMPLE 47

A disc of woollen material [10 cm$^2$] is sprayed with an acetonic solution of the active substance, and the disc, together with an untreated disc of material and a disc of material soaked only with acetone, are each hung in a cage occupied by 20 young cloths moth (*Tineola biselliella*).

The development of the eggs layed at 25° C. is registered for 4 days. 100% sterilant action: larvae hatch from none of the eggs laid on treated and untreated discs of woollen material. 100% ovicidal action: larvae hatch from none of the eggs laid on treated discs of woollen material.

| Active substance | Amount of active substance $10^{-x}$g/cm$^2$ | Sterilant action % | Ovicidal action % |
|---|---|---|---|
| VI | $10^{-3}$ | 0 | 100 |
|  | $10^{-4}$ | 0 | 100 |
| Control with acetone | | 0 | 0 |
| Control with acetone | | 0 | 0 |

EXAMPLE 48

A filter paper strip [90 cm$^2$] is sprayed with an acetonic solution of the active substance and, after drying, the strip, together with an untreated paper strip and a paper strip soaked only with acetone, are each occupied by 3–4 pairs of freshly moulted images of the cotton bug (*Dysdercus cingulatus*).

The development of the eggs laid daily is registered. 100% mortality of the eggs: no development of the embryos in the eggs laid on strips soaked with active substance.

| Active substance | Amount of active substance $10^{-x}$g/cm$^2$ | Number of eggs | Number of larvae | Mortality % |
|---|---|---|---|---|
| I | $10^{-5}$ | 380 | — | 100 |
|  | $10^{-6}$ | 50 | — | 100 |
| II | $10^{-5}$ | 430 | — | 100 |
| III | $10^{-5}$ | 311 | 4 | 99 |
| IV | $10^{-5}$ | 392 | 60 | 83 |
| Control with acetone | | 270 | 262 | 3 |
| Control with acetone | | 41 | 390 | 5 |

EXAMPLE 49

1 g of p-[(3-methyl-2-butenyl)oxy]-α-(2-propynyloxy)toluene was dissolved in a mixture of 80 ml of dioxane and 40 ml of water. To this solution there was added under cooling with ice (10° C.) portionwise 0.85 g of N-bromosuccinimide. After this addition the mixture was stirred at room temperature for 15 hours and then diluted with 80 ml of water. Thereafter 2.5 g of sodium sulfite are added and the solution exhaustively extracted with ether. The combined ether extracts were washed with water, dried over sodium sulfate and evaporated. By chromatography on Kieselgel with hexane/ethyl acetate (85:15 parts by volume) there was obtained p-[(3-bromo-2-hydroxy-3-methylbutyl)oxy]-α-(2-propynyloxy)toluene. $n_D^{22}$: 1.5374.

We claim:
1. A compound of the formula

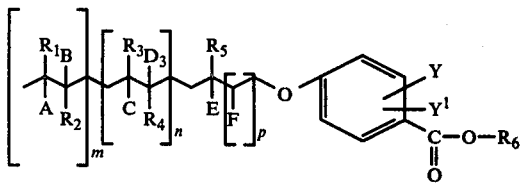

wherein A, B, C, D, E, and F are individually hydrogen, or A and B taken together form a carbon to carbon bond, C and D taken together form a carbon to carbon bond, E and F taken together form a carbon to carbon bond; $R_1$, $R_3$ and $R_5$ are methyl or ethyl;

Y and Y$^1$ are hydrogen, halogen, lower alkyl or lower alkoxy; $R_2$ and $R_4$ are hydrogen or methyl; $R_6$ is lower alkynyl; and m, n and p are integers of from 0 to 1; with at least one of m, n and p being 1; with the proviso that A, B, C, D, E and F are not all hydrogen.

2. The compound of claim 1 having the formula:

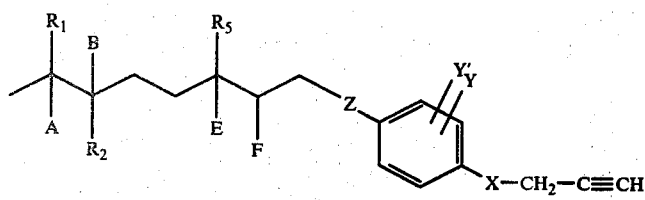

wherein $R_1$, $R_2$, $R_5$, A, B, E, F, Y, Y' Z and X are as above.

3. The compound of claim 2 wherein E and F are a carbon to carbon bond.

4. The compound of claim 3 wherein said compound is p-[(3,7-dimethyl2,6-octadienyl)-oxy]benzoic acid propargyl ester.

5. The compound of claim 2 wherein A and B taken together are a carbon to carbon bond and E and F taken together are a carbon to carbon bond.

6. The compound of claim 5 wherein said compound is 4-[(3,7-dimethyl-2,6-octadienyl)-oxy]-3,5-methoxybenzoic acid propargyl ester.